(12) United States Patent
Mastorakis

(10) Patent No.: US 11,730,893 B2
(45) Date of Patent: Aug. 22, 2023

(54) INJECTION DEVICE

(71) Applicant: NUMEDICO TECHNOLOGIES (IP) PTY LTD., Adelaide SA (AU)

(72) Inventor: Emmanuel Mastorakis, Monte-Carlo (MC)

(73) Assignee: Numedico Technologies (IP) Pty Ltd., Adelaide (AU)

( * ) Notice: Subject to any disclaimer, the term of this patent is extended or adjusted under 35 U.S.C. 154(b) by 274 days.

(21) Appl. No.: 16/314,294

(22) PCT Filed: May 17, 2017

(86) PCT No.: PCT/EP2017/061782
§ 371 (c)(1),
(2) Date: Dec. 28, 2018

(87) PCT Pub. No.: WO2018/001625
PCT Pub. Date: Jan. 4, 2018

(65) Prior Publication Data
US 2021/0052824 A1 Feb. 25, 2021

(30) Foreign Application Priority Data
Jun. 29, 2016 (FR) ...................................... 1656054

(51) Int. Cl.
*A61M 5/32* (2006.01)
(52) U.S. Cl.
CPC .................................. *A61M 5/322* (2013.01)
(58) Field of Classification Search
CPC .. A61M 5/322; A61M 5/3221; A61M 5/3232; A61M 2005/3231;
(Continued)

(56) References Cited

U.S. PATENT DOCUMENTS

| 4,804,370 A | 2/1989 | Haber et al. |
| 5,328,475 A | 7/1994 | Chen |

(Continued)

FOREIGN PATENT DOCUMENTS

| CA | 160617 S | 2/2015 |
| EP | 1244484 B1 | 11/2003 |

(Continued)

OTHER PUBLICATIONS

International Search Report from corresponding International Application No. PCT/EP2017/061782, dated Jul. 27, 2017, pp. 1-3, European Patent Office, Rijswijk, The Netherlands.

(Continued)

*Primary Examiner* — Kevin C Sirmons
*Assistant Examiner* — Alexandra Lalonde
(74) *Attorney, Agent, or Firm* — Bodman PLC

(57) ABSTRACT

An injection device, comprising an interface for mounting on a syringe body, the interface comprising an internal passage delimited by an inner wall, a needle and a sheath for receiving said needle, said sheath comprising an outer wall provided with a contact portion of said sheath in contact with an attachment portion of the inner wall of the interface, wherein the contact portion comprises a first bead and in that the attachment portion comprises a second bead, the first and second beads each forming a ring protruding respectively on the contact portion and the attachment portion, the first bead being in contact with the second bead.

19 Claims, 2 Drawing Sheets

(58) Field of Classification Search
CPC .. A61M 5/31515; A61M 5/3234; A61M 5/32;
A61M 5/178; A61M 5/321; A61M
5/3205; A61M 5/3293; A61M 5/34;
A61M 5/344; A61M 5/345; A61M 5/346;
A61M 5/348; A61M 5/349; A61M
2005/3103; A61M 2005/3117; A61M
2005/3118; A61M 2005/3206; A61M
2005/3223; A61M 2005/3224; A61M
2005/3226; A61M 2005/323; A61M
2005/3235; A61M 2005/3239
See application file for complete search history.

(56) References Cited

U.S. PATENT DOCUMENTS

| | | | |
|---|---|---|---|
| 5,575,774 | A | 11/1996 | Chen |
| 6,669,666 | B2 | 12/2003 | Lu |
| D579,561 | S | 10/2008 | Call et al. |
| D618,347 | S | 6/2010 | Bradshaw |
| D621,929 | S | 8/2010 | Van Der Stappen |
| D623,738 | S | 9/2010 | Van Der Stappen |
| D669,579 | S | 10/2012 | Marshall et al. |
| D689,601 | S | 9/2013 | Black et al. |
| D779,057 | S | 2/2017 | Wohlfahrt et al. |
| D783,816 | S | 4/2017 | Wohlfahrt et al. |
| D789,528 | S | 6/2017 | Wohlfahrt et al. |
| D823,459 | S | 7/2018 | Bendek et al. |
| 2004/0014876 | A1 | 1/2004 | Ichikawa et al. |
| 2004/0210198 | A1* | 10/2004 | Shih .............. A61M 5/322 604/218 |
| 2006/0253074 | A1 | 11/2006 | Thayer |
| 2008/0027381 | A1 | 1/2008 | Smith et al. |
| 2013/0116619 | A1 | 5/2013 | Chen |
| 2013/0331817 | A1 | 12/2013 | Woehr |
| 2014/0296782 | A1 | 10/2014 | Ulrich et al. |
| 2014/0330217 | A1* | 11/2014 | Thorley ............ A61M 5/3232 604/198 |
| 2017/0072142 | A1 | 3/2017 | Perthu |

FOREIGN PATENT DOCUMENTS

| | | |
|---|---|---|
| EP | 1551481 A2 | 7/2005 |
| EP | 1551481 B1 | 4/2009 |
| EP | 2589400 A2 | 5/2013 |
| EP | 2589400 B1 | 12/2018 |
| GB | 90014623290001 | 11/2014 |
| RU | 2012145660 A | 4/2014 |
| WO | 9107198 A1 | 5/1991 |
| WO | 2004014470 A1 | 2/2004 |
| WO | 2006047810 A1 | 5/2006 |
| WO | 2007123826 A2 | 11/2007 |
| WO | 2013067588 A1 | 5/2013 |

OTHER PUBLICATIONS

"A. Titan: ASPR-a Premium Syringe." Found online at Amazon.com. Nov. 21, 2022. Reference dated Jun. 10, 2014. Retrieved from https://www.amazon.com/Titan-ASPR-1-Premium-Aspirating-Syringe/dp/B00JGITH4W.

"Drug Development: Special Feature." Found online at drug-dev.com. Nov. 21, 2022. Reference dated Sep. 2012. Retrieved from https://drug-dev.com/special-feature-handheld-injection-devices-safer-simpler-and-more-customized/.

"Artman Instruments: Aspirating Dental Syringes." Found online atAmazon.com. Nov. 21, 2022. Reference dated Aug. 14, 2016. Retrieved from https://www.amazon.com/Aspirating-Dental-Syringes-Handle-Linkers/dp/B06XGXLVVM.

"MIT News: Device may inject a variety of drugs without using needles." Found online at news.mit.edu. Nov. 21, 2022. Reference dated May 24, 2012. Retrieved from https://news.mit.edu/2012/needleless-injections-0524.

International Search Report for application No. PCT/EP2017/061781; dated Jul. 18, 2017; 3 pp.

* cited by examiner

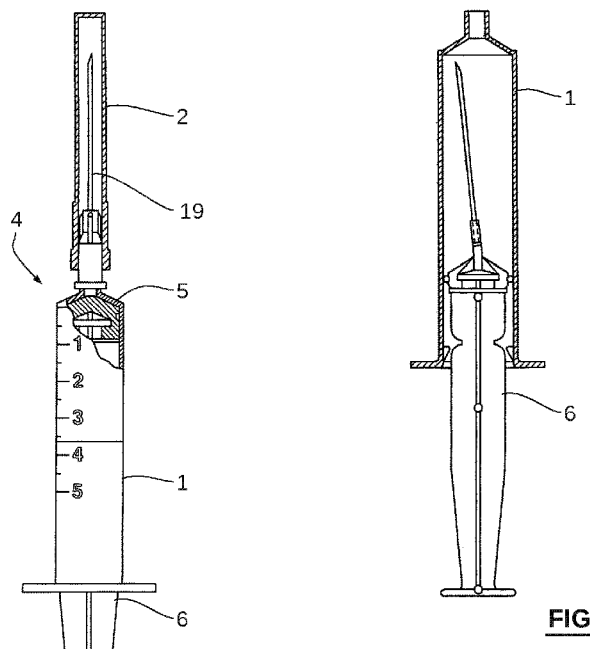
FIG 1
PRIOR ART
FIG 2
PRIOR ART
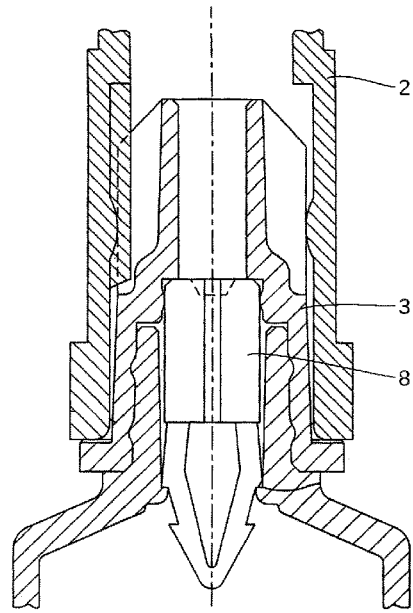
FIG 3
PRIOR ART

INJECTION DEVICE

FIELD OF THE INVENTION

This invention relates to an injection device and a syringe provided with such a device.

A preferred application is in the medical devices and accessories industry.

TECHNOLOGICAL BACKGROUND

In the medical field, devices are known to enable injections to be carried out using a needle, this term being understood here as any pointed device enabling a fluid to pass therein towards the human or animal body in particular. In particular, such a device in the form of a syringe comprising a body and a piston that can slide in the body is known from document WO 2004/014470 A1. In addition, to carry out the injection, the syringe includes an injection device attached to the head of the syringe body and provided with a needle. Such a device is illustrated in FIGS. 1 to 3. The device attached to the head of the syringe body comprises a part enabling it to be mounted on said body, as a mechanical interface and a part which the needle is assembled on, forming the sheath receiving this needle. The sheath and the interface are in mutual contact. Nevertheless, according to this anteriority, the needle is retractable into the syringe body once the injection operations are completed. This provision provides greater safety of use for the medical device. To achieve this retraction, the sheath carrying the needle is disconnected from the interface as shown in FIG. 2. The fact that the sheath and interface must move from a position where they are secured together and sealed to a position where they are disconnected raises sealing issues that are generally solved by separately applied O-rings.

The sealing techniques used in this way seriously increase the complexity of the assembly of the devices and their costs.

A retractable syringe is also known from document WO AI 2013/067588, in which FIG. 10 shows a mechanical retention of a sheath secured to the needle with a base part; the base part has a protrusion that fits into a recess in the sheath; this contact of a protrusion in a recess is not very effective in terms of sealing.

The present invention makes it possible to solve all or at least some of the drawbacks of the current techniques.

SUMMARY OF THE INVENTION

An aspect of the invention relates to an injection device, comprising an interface for mounting on a syringe body, with the interface comprising an internal passage delimited by an inner wall, a needle and a sheath for receiving the needle, with said sheath comprising an outer wall provided with a contact portion of said sheath against an attachment portion of the inner wall of the interface Advantageously, the contact portion includes a first bead and the attachment portion includes a second bead, with the first and second beads each forming a ring protruding respectively on the contact portion and the attachment portion, with the first bead being in contact with the second bead.

The invention also relates to a syringe with a body, a piston capable of sliding in the body, and a device as described above.

According to one aspect, a third bead is present so that one of the beads is framed by two beads. There is therefore a lateral contact on either side of a bead; this assembly is more efficient to stop the translation of the sheath relative to the interface; and it is less hyperstatic than those existing because two contacts with a reduced surface area around the central bead are provided. The contact between two beads can be along a line so that sizing or adjustment problems are reduced. This solution is much more efficient than those known in which a bead is inserted into a recess.

BRIEF DESCRIPTION OF THE FIGURES

Other characteristics, aims and advantages of the present invention will appear upon reading the following detailed description and referring to the appended drawings given as non-limiting examples and wherein:

FIG. 1 shows an overview of a syringe according to the state of the art described in document WO 2004/014470 A1;

FIG. 2 is a view of this state of the art, showing a retracted position of the needle;

FIG. 3 is a detailed view of this state of the art showing the cooperation between the interface and the sheath of the device mounted on the top of the syringe.

DETAILED DESCRIPTION

Figure 4:
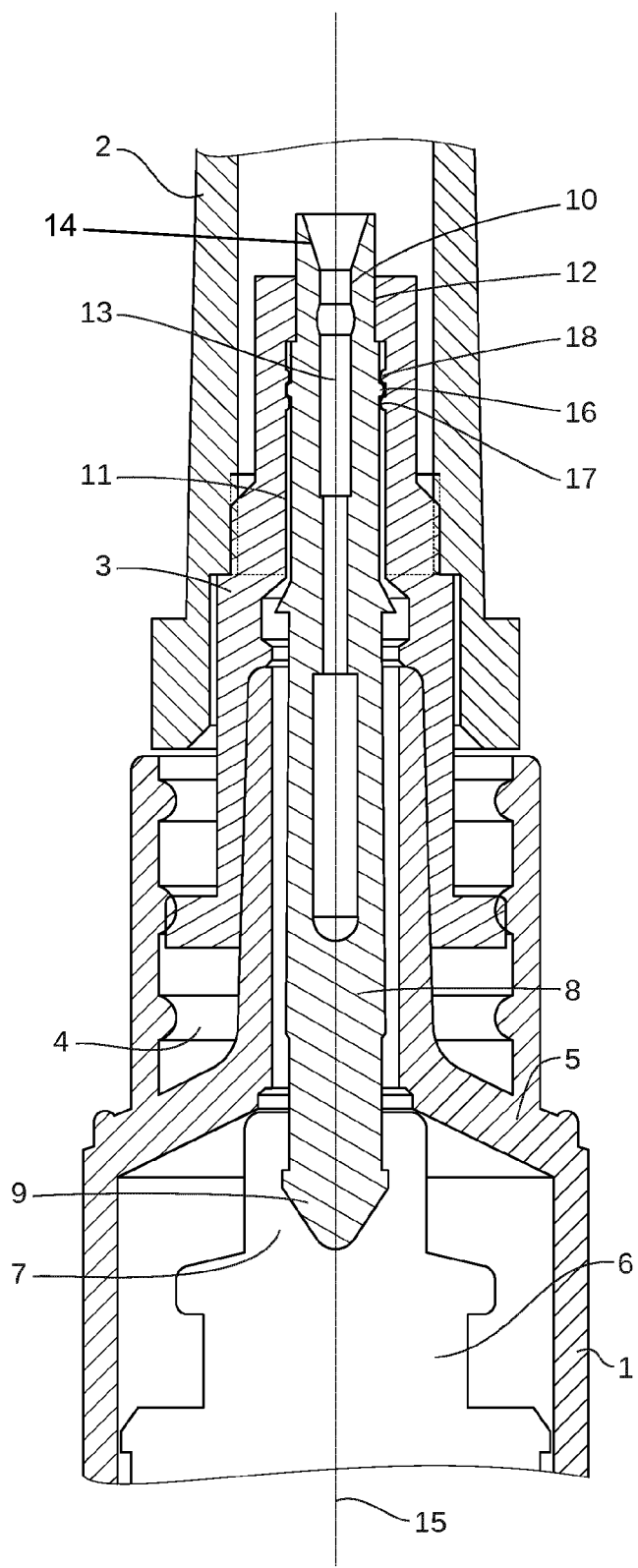
FIG. 4 is a sectional view of one embodiment of the invention.

Prior to going into details relating to the preferred embodiments of the invention while referring more particularly to the drawings, other optional characteristics of the invention which may be implemented in any combination or alternately, are mentioned hereafter:

- one of the contact portion or the attachment portion has a third bead 18;
- the third bead 18 and the other bead of the one of the contact portion or the attachment portion which includes the third bead 18, frame the bead of the other one of the contact portion and the attachment portion;
- the bead of the other one of the contact portion and the attachment portion is in contact with both the third bead 18 and the other bead of the other one of the contact portion and the attachment portion which includes the third bead 18;
- the contact portion comprises only the first bead 16, and the attachment portion comprises the second bead 17 and the third bead 18;
- the contact portion is cylindrical around the first bead 16;
- the attachment portion is cylindrical around the second bead 17;
- at least one of the beads has an arc-shaped longitudinal section;
- the sheath 8 comprises an inner channel 13 including a seat 10 so configured as to accommodate a proximal end of the needle 19, with said channel 13 having a section extending beyond the end of the contact portion opposite the seat 10, with said section having a transverse opening 14;
- the sheath 8 is mounted sliding relative to the interface 3, with the beads forming stops against sliding; and
- the device comprises no O-ring between the sheath 8 and the interface 3.

For the proper understanding of the invention, the following definitions shall apply:

- longitudinal direction 15: the long dimension of the syringe and/or injection device; generally speaking, the body of the syringe and possibly any other part of the invention may have symmetry around the longitudinal direction;

transverse and lateral mean a direction perpendicular to the longitudinal direction 15; and needle means any pointed device used to perform an injection function, in particular the injection of fluid into the human or animal body.

The state of the art device shown in FIG. 1 typically comprises a syringe body 1 here essentially cylindrical in shape and having a proximal end with a mouthpiece for receiving a piston 6 and an opposite distal end for receiving an injection device with a needle. At its distal end, the body 1 has a narrowed section head produced by a shoulder 5. Advantageously, the injection device is provided with a cap during storage. This provides protection to the needle 19.

FIG. 2 shows the needle 19 retraction function. To achieve this, the piston 6 has, at its distal end, a device enabling it to cooperate with a portion of the injection device which the needle 19 is mounted on. Thus, when the piston 6 is sufficiently deep into the body 1, it is docked to the part secured to the needle 19 and a subsequent sliding action of the piston 6 tending to pull it out of the body 1 enables the needle 19 to be retracted from inside the body 1 as shown in FIG. 2. As shown in FIG. 2, a reduced cross-section of the piston 6 may provide a breakable area so as to break the piston and avoid excessive dimensions in this position. It is easy to understand that the needle 19 is thus protected, which offers greater safety than the most conventional syringes.

FIG. 3 is a detailed drawing illustrating, according to the state of the art, a possible mounting of the needle. In this figure, an interface 3 is mounted at the head of the body 1 and cooperates with a sheath 8 provided with an inner channel for receiving the needle 19. At its end opposite the receiving area of the needle 19, the sheath 8 has means for securing with the distal end of the piston 6. The contact between the interface 3 and the sheath 8 is provided without any particular provision as regards sealing, which may lead to leaks or the need for an additional seal.

As a counterpoint to what is shown in FIGS. 1 to 3, FIG. 4 presents a non-exhaustive embodiment of the invention.

The interface 3 has an internal passage delimited by an inner wall 11. A proximal portion of this passage can be used to mount the device of the invention on the head 4 of a syringe. In the case illustrated, the head 4 also has a double wall for cooperating with the interface 3. The internal passage of the interface 3 also receives the sheath 8, which extends in the longitudinal direction 15. Advantageously, a channel 13 inside the sheath 8 enables the fluid to flow therethrough in order to supply the needle 19 arranged at an upper portion as a seat 10 of the sheath 8. At this seat 10, a cylinder-to-cylinder branch is advantageously formed with the proximal end of the needle 19. Between these two ends, the sheath 8 is secured to the interface 3. More precisely, a contact portion of the outer wall 12 of the sheath 8 cooperates with an attachment portion of the inner wall 11 of the interface 3. This cooperation is advantageously removable so as to enable a retracted configuration of the device as shown in the example of FIG. 2. Thus, the securing of the sheath 8 in the interface 3 can be so configured as to be overcome by a sufficient force, especially from a user during a phase of action on the piston, driving the sheath 8 once it is docked at the end of piston 6.

To obtain this assembly, beads 16, 17, 18 are formed, according to the invention, on the contact portion and the attachment portion of the sheath 8 and the interface 3. An example of the forming of such beads is illustrated in FIG. 4. Beads mean a part protruding relative to the rest of the peripheral surface of the portion under consideration, with such portion extending as a ring forming a continuous belt at a certain level in the longitudinal direction 15. For example, the bead may have an arc-shaped section as in the case shown in FIG. 4.

At a minimum, two beads are each formed on one of the sheath 8 and the interface 3. Thus, FIG. 4 shows a first bead 16 on the outer wall of the sheath 8 and a second bead 17 on the inner wall of the interface 8. The beads 16, 17 are so configured as to press against each other in order to produce a cooperation surface enabling an optimized sealing. In addition, the combination of these beads makes it possible to form a stop opposing, at least without the exercise of an external tensile force, the relative sliding of the two parts. In the case shown, a third bead 18 is made, here on the interface 3. Advantageously, the bead 16 is framed by the second and the third beads 17, 18. The bead 16 is preferably in simultaneous contact with the other two beads. It should be understood that this arrangement precisely immobilizes the sheath 8 and ensures a double contact that prevents leaks.

Advantageously, the rest of the contact portion and the attachment portion of the sheath 8 and the interface 3 is not protruding around the beads 16, 17, 18. Thus, the stop and seal function is concentrated on these beads.

According to a possible embodiment illustrated in FIG. 4, the sheath 8 has, in the area of securing with the interface 3 (including the beads), a cylindrical outer wall (it can also be tapered) which the bead(s) carried by the sheath 8 protrude(s) on. Similarly, the inner wall of the interface 3 has a cylindrical shape (it can also be tapered) in the area of securing to the interface 3, which the bead(s) carried by the interface 3 protrude(s) on.

Cooperation is thus preferably centred on areas having circular cross-sections and the beads are projections protruding from a base surface having a circular cross-section. The beads then cooperate in small contact areas, mainly circular lines. There may be no further contact between the sheath and the interface in the area where the beads are present, or even no further contact stopping the translation between the sheath and the interface along their length.

It is desirable for the beads to be so configured that they only come into contact with each other, and not with other parts of the sheath and the interface.

Generally speaking, the beads are all protruding relative to the portion of the sheath or the interface that carries them. Preferably, the portion that carries two beads includes an intermediate area between these beads, with this area being cylindrical in shape and/or so configured that there is no contact between this area and the bead of the other portion.

It should be noted, in the case shown in FIG. 4, that the sheath 8 extends through the entire interface 3 so that it opens at a distal end on which the seat 10 is formed, and at a proximal end inside the syringe body 1. A channel 13 advantageously extends throughout the sheath 8, so as to enable a fluid to flow from the storage area inside the body 1 to the injection needle 19. Preferably, in at least a portion of the length of the sheath 8, the channel 13 opens laterally so that the fluid can be admitted inside same. These can be transverse apertures enabling the fluid to enter when compressed by the action of the piston. The fluid can then pass through the rest of the channel 13 until it exits out of the syringe. Advantageously, the sheath 8 extends short of the proximal end of the interface 3 towards the body 1 and penetrates into the main volume of the body 1, below the shoulder 5.

The components of the sheath 8 and the interface 3 are preferably each solid and made of a single piece of material, this material being preferably a plastic material. It should be understood that the beads can easily be manufactured completely with each of these parts, by conformation, especially when moulding same.

REFERENCES

1. Syringe body
2. Cap
3. Interface
4. Head
5. Shoulder
6. Piston
7. Securing area
8. Sheath
9. Proximal end
10. Seat
11. Inner wall
12. Outer wall
13. Channel
14. Transverse opening
15. Longitudinal direction
16. First bead
17. Second bead
18. Third bead
19. Needle

The invention claimed is:

1. An injection device, comprising an interface for mounting on a syringe body, the interface comprising an internal passage delimited by an inner wall, a needle and a sheath for receiving said needle, said sheath comprising an outer wall provided with a contact portion of said sheath in contact with an attachment portion of the inner wall of the interface, wherein:
the contact portion comprises a first bead forming a first ring protruding from the outer wall of the sheath;
the attachment portion comprises a second bead forming a second ring protruding from the inner wall of the interface and a third bead forming a third ring protruding from the inner wall of the interface, wherein the attachment portion further comprises an intermediate area between the second bead and the third bead, wherein the intermediate area is cylindrical in shape;
wherein the third bead and the second bead of the attachment portion frame the first bead of the contact portion; and
wherein the first bead of the contact portion is in contact with the third bead in a first contact area that is a circular line and forms a first seal between the first bead and the third bead and is in contact with the second bead of the attachment portion in a second contact area that is another circular line and forms a second seal between the first bead and the second bead, but is not in contact with the intermediate area of the attachment portion.

2. The injection device according to claim 1, wherein the contact portion is cylindrical around the first bead.

3. The injection device according to claim 1, wherein the attachment portion is cylindrical around the second bead.

4. The injection device according to claim 1, wherein at least one of the first, second or third beads has an arc-shaped longitudinal section.

5. The injection device according to claim 1, wherein the sheath comprises an inner channel including a seat configured to accommodate a proximal end of the needle, with said inner channel having a section extending beyond an end of the contact portion opposite the seat, with said section having a transverse opening.

6. The injection device according to claim 1, in which the sheath is mounted sliding relative to the interface, with the first, second and third beads forming stops opposing sliding.

7. The injection device according to claim 1, not comprising any O-ring between the sheath and the interface.

8. The injection device according to claim 1, wherein the inner wall of the interface distal to the attachment portion is free of contact with the outer wall of the sheath.

9. The injection device according to claim 1, wherein the first bead, the second bead, and the third bead are convex to provide the first contact area between the first bead and the second bead and to provide the second contact area between the first bead and the third bead.

10. The injection device according to claim 9, wherein the first bead, the second bead and the third bead are arc-shaped in cross-section.

11. The injection device according to claim 1, wherein the attachment portion is monolithic and includes the inner wall, the second bead, and the third bead.

12. The injection device according to claim 1, wherein the outer wall of the sheath and the inner wall of the interface are both one of cylindrical or tapered.

13. The injection device according to claim 12, wherein the second bead and the third bead extend from the inner wall toward the contact portion a same length.

14. The injection device according to claim 1, wherein the first bead, the second bead, and the third bead are convex to provide the first contact area between the first bead and the second bead and to provide the second contact area between the first bead and the third bead; wherein the first bead, the second bead, and the third bead are arc-shaped in cross-section;
wherein the attachment portion is monolithic and includes the inner wall, the second bead, and the third bead; and
wherein the outer wall of the sheath and the inner wall of the interface are both one of cylindrical or tapered; and
wherein the second bead and the third bead extend from the inner wall toward the contact portion a same length.

15. A syringe with a body, a piston capable of sliding in the body, and the injection device according to claim 1.

16. The syringe according to claim 15, wherein the interface is mounted on the syringe body.

17. The syringe according to claim 15, wherein the first bead, the second bead, and the third bead are convex to provide the first contact area between the first bead and the second bead and to provide the second contact area between the first bead and the third bead; and
wherein the first bead, the second bead, and the third bead are arc-shaped in cross-section.

18. The syringe according to claim 15, wherein the attachment portion is monolithic and includes the inner wall, the second bead, and the third bead.

19. The syringe according to claim 15, wherein the outer wall of the sheath and the inner wall of the interface are both one of cylindrical or tapered; and wherein the second bead and the third bead extend from the inner wall toward the contact portion a same length.

* * * * *